(12) United States Patent
Matsui et al.

(10) Patent No.: US 6,391,604 B1
(45) Date of Patent: May 21, 2002

(54) THERMOSTABLE ENZYME HAVING PHOSPHATIDYLETHANOLAMINE N-METHYLTRANSFERASE ACTIVITY

(75) Inventors: Ikuo Matsui; Kazuhiko Ishikawa; Hiroyasu Ishida; Yoshitsugu Kosugi, all of Ibaraki; Yasutaka Tahara, Shizuoka, all of (JP)

(73) Assignee: Agency of Industrial Science and Technology, Tokyo (JP)

( * ) Notice: Subject to any disclaimer, the term of this patent is extended or adjusted under 35 U.S.C. 154(b) by 0 days.

(21) Appl. No.: 09/519,729

(22) Filed: Mar. 3, 2000

(30) Foreign Application Priority Data

Mar. 30, 1999 (JP) .......................................... 11-089312

(51) Int. Cl.$^7$ ............................ C12N 9/10; C12N 1/20; C12N 15/00; C07H 21/04; C07K 1/00
(52) U.S. Cl. ................. 435/193; 435/252.3; 435/320.1; 435/822; 536/23.2; 530/350
(58) Field of Search .............................. 435/193, 252.3, 435/320.1, 822; 536/23.2; 530/350

(56) References Cited

FOREIGN PATENT DOCUMENTS

WO    WO 85/00817    2/1985

OTHER PUBLICATIONS

Bowie et al., 1990. Science, vol. 247, pp. 1306–1310,.*
Arondel et al., "Isolation and functional expression in *Escherichia coli* of a gene encoding phosphatidylethanolamine methyltransferase (EC 2.1.1.17) form *Rhodobacter sphaeroides*," *J. Biol. Chem.*, 268:16002–16008 (1993).
Ausubel et al., *Short Protocols in Molecular Biology: A Compendium of Methods from Current Protocols in Molecular Biology*, Third Edition, John Wiley & Sons, Inc. (1992).
Cui et al., "Cloning and expression of a novel phosphatidylethanolamine N–methyltransferase," *J. Biol. Chem.*, 268:16655–16663 (1993).

Kawarabayasi et al., "Complete Sequence and Gene Organization of the Genome of a Hyper–thermophilic Archaebacterium, *Pyrococcus horikoshii* OT3,"DNA Research 5(2):55–76 (1998).
Kodaki et al., "Yeast Phosphatidylethanolamine Methylation Pathway," J. Biol. Chem., 262:15428–15435 (1987).
Mark et al., "Site–specific mutagenesis of the human fibroblast interferon gene," Proc. Natl. Acad. Sci. USA 81:5662–5666 (1984).
"Protein, Nucleic Acid and Enzyme," 41(5):415–445 (1996). The reference provided to the Examiner is in the Japanese language. This reference describes conventional PCR techniques including PCR methods (e.g., long PCR, hot start PCR, RACE, nested PCR, etc.), PCR reaction conditions for denaturation, annealing, extension, etc., and design of PCR primers.
Sambrook et al., Molecular Cloning: A Laboratory Manual, Second Edition, Cold Spring Harbor Laboratory Press (1989);
Sanger et al., "DNA sequencing with chain–terminating inhibitors," Proc. Natl. Sci. USA 74:5463–5467 (1977).
Tahara et al., "Properties of Phosphatidylethanolamine N–methyltransferase from Hyper–thermophilic Archaeon *Pyrococcus horikshii*," Nippon Nogeikagaku Kaishi, vol. 73, Suppl. (Annual Meeting, Mar. 30–Apr. 1, 1999).

* cited by examiner

*Primary Examiner*—Ponnathapura Achutamurthy
*Assistant Examiner*—Tekchand Saidha
(74) *Attorney, Agent, or Firm*—Medlen & Carroll, LLP (57) ABSTRACT

A thermostable phosphatidylethanolamine N-methyltransferase and a process for producing the enzyme are provided. A host cell is transformed with an expression vector containing DNA encoding a thermostable enzyme derived from hyper-thermophilic archaea such as Pyrococcus, the enzyme having phosphatidylethanolamine N-methyltransferase activity and an optimum temperature of 90° C. or higher, and the transformed host cell is cultured.

29 Claims, 6 Drawing Sheets

FIG. 1

```
        10         20         30         40         50         60
TTGAGTTATAGGGAGAAGTACAATAGAATAGGATCCAAGTATGATATTCTAGAGTCTCCA
 L  S  Y  R  E  K  Y  N  R  I  G  S  K  Y  D  I  L  E  S  P 70         80         90        100        110        120
TTGGAGAGATACTTTGAGCCACTGAGAAAGAAAGCTGTTAGCTTGGTTAGAGGTAAAGTT
 L  E  R  Y  F  E  P  L  R  K  K  A  V  S  L  V  R  G  K  V 130        140        150        160        170        180
CTGGAGATAGGTATCGGAACCGGGAAAACGCTAAAATACTATCCAAATGATGTTCAGCTT
 L  E  I  G  I  G  T  G  K  T  L  K  Y  Y  P  N  D  V  Q  L 190        200        210        220        230        240
TACGCAATTGATGGAAGCGAGGAGATGCTTAAAGTAGCAAGGGAAAAAGCGAGACAACTT
 Y  A  I  D  G  S  E  E  M  L  K  V  A  R  E  K  A  R  Q  L 250        260        270        280        290        300
GGGATCAATGTAAAGTTCTTTAAAGCGGAAGCTGAGGATCTACCTTTTCCTAACGACTTT
 G  I  N  V  K  F  F  K  A  E  A  E  D  L  P  F  P  N  D  F 310        320        330        340        350        360
TTCGACTTCGTAATTTCATCTTTCGTCTTCTGCACAATTCCAAATCCGAAGAAGGCCATG
 F  D  F  V  I  S  S  F  V  F  C  T  I  P  N  P  K  K  A  M 370        380        390        400        410        420
AGGGAGATAATAAGAGTTTTAAAGCCAAGCGGAAAGGTCATATTCCTTGAACATACGCTC
 R  E  I  I  R  V  L  K  P  S  G  K  V  I  F  L  E  H  T  L 430        440        450        460        470        480
AGCGATAGCTTCCTAATAAACATGCTATTTCTAGCACCATTAGAGCTTATATTAAGACCT
 S  D  S  F  L  I  N  M  L  F  L  A  P  L  E  L  I  L  R  P 490        500        510        520        530        540
TTAATAGATGACAGCACTACCAGAGAAACCCACAAGCTTGTGAGAAAATTCTTCAGAGTG
 L  I  D  D  S  T  T  R  E  T  H  K  L  V  R  K  F  F  R  V 550        560        570        580        590        600
GAGAGGGAAGAGAGCTACTATAAGGGGATTGTGAGGTTCATAGTGGCCAGGCCATTGTGG
 E  R  E  E  S  Y  Y  K  G  I  V  R  F  I  V  A  R  P  L  W

TGA
 *
```

FIG. 2

PE methylation pathway and CDP-choline pathway

FIG. 3

Substrate specificity of PE N-methyltransferase

FIG. 4

Effect of temperature on PE N-methyl-transferase

FIG. 5

Effect of pH on PE N-methyltransferase

FIG. 6

Thermostability of PE N-methyltransferase

SEQUENCE LISTING

<160> NUMBER OF SEQ ID NOS: 4

<210> SEQ ID NO 1
<211> LENGTH: 200
<212> TYPE: PRT
<213> ORGANISM: Pyrococcus horikoshii

<400> SEQUENCE: 1

```
Lys Ser Tyr Arg Glu Lys Tyr Asn Arg Ile G ly Ser Lys Tyr Asp Ile
 1               5                   10                  15

Leu Glu Ser Pro Leu Glu Arg Tyr Phe Glu P ro Leu Arg Lys Lys Ala
             20                  25                  30

Val Ser Leu Val Arg Gly Lys Val Leu Glu I le Gly Ile Gly Thr Gly
         35                  40                  45

Lys Thr Leu Lys Tyr Tyr Pro Asn Asp Val G ln Leu Tyr Ala Ile Asp
     50                  55                  60

Gly Ser Glu Glu Met Leu Lys Val Ala Arg G lu Lys Ala Arg Gln Leu
 65                  70                  75                  80

Gly Ile Asn Val Lys Phe Phe Lys Ala Glu A la Glu Asp Leu Pro Phe
                 85                  90                  95

Pro Asn Asp Phe Phe Asp Phe Val Ile Ser S er Phe Val Phe Cys Thr
             100                 105                 110

Ile Pro Asn Pro Lys Lys Ala Met Arg Glu I le Ile Arg Val Leu Lys
         115                 120                 125

Pro Ser Gly Lys Val Ile Phe Leu Glu His T hr Leu Ser Asp Ser Phe
     130                 135                 140
```

```
-continued

Leu Ile Asn Met Leu Phe Leu Ala Pro Leu Glu Leu Ile Leu Arg Pro
145                 150                 155                 160

Leu Ile Asp Asp Ser Thr Thr Arg Glu Thr His Lys Leu Val Arg Lys
                165                 170                 175

Phe Phe Arg Val Glu Arg Glu Ser Tyr Tyr Lys Gly Ile Val Arg
            180                 185                 190

Phe Ile Val Ala Arg Pro Leu Trp
        195                 200

<210> SEQ ID NO 2
<211> LENGTH: 600
<212> TYPE: DNA
<213> ORGANISM: Pyrococcus horikoshii

<400> SEQUENCE: 2
ttgagttata gggagaagta caatagaata ggatccaagt atgatattct a gagtctcca    60 ttggagagat actttgagcc actgagaaag aaagctgtta gcttggttag a ggtaaagtt   120 ctggagatag gtatcggaac cgggaaaacg ctaaaatact atccaaatga t gttcagctt   180 tacgcaattg atggaagcga ggagatgctt aaagtagcaa gggaaaaagc g agacaactt   240 gggatcaatg taaagttctt taaagcggaa gctgaggatc tacctttttcc t aacgacttt   300 ttcgacttcg taatttcatc tttcgtcttc tgcacaattc caaatccgaa g aaggccatg   360 agggagataa taagagtttt aaagccaagc ggaaaggtca tattccttga a catacgctc   420 agcgatagct tcctaataaa catgctattt ctagcaccat tagagcttat a ttaagacct   480 ttaatagatg acagcactac cagagaaacc cacaagcttg tgagaaaatt c ttcagagtg   540 gagagggaag agagctacta taagggggatt gtgaggttca tagtggccag g ccattgtgg   600

<210> SEQ ID NO 3
<211> LENGTH: 67
<212> TYPE: DNA
<213> ORGANISM: Artificial Sequence
<220> FEATURE:
<223> OTHER INFORMATION: Description of Artificial  Sequence:  Synthetic

<400> SEQUENCE: 3
ttttgaattc ttacatatga gttataggga gaagtacaat agaatagggt c caagtatga    60 tattcta                                                               67

<210> SEQ ID NO 4
<211> LENGTH: 42
<212> TYPE: DNA
<213> ORGANISM: Artificial Sequence
<220> FEATURE:
<223> OTHER INFORMATION: Description of Artificial  Sequence:  Synthetic

<400> SEQUENCE: 4
ttttggtacc tttggatcct taagccatcg atcaccacaa tg                        42
```

THERMOSTABLE ENZYME HAVING PHOSPHATIDYLETHANOLAMINE N-METHYLTRANSFERASE ACTIVITY

FIELD OF THE INVENTION

The present invention relates to a thermostable phosphatidylethanolamine N-methyltransferase, DNA encoding the enzyme and a process for producing the enzyme. Enzymes of the present invention may be useful for synthesis of a polar lipid with high optical purity and the like.

PRIOR ART

Figure 2:
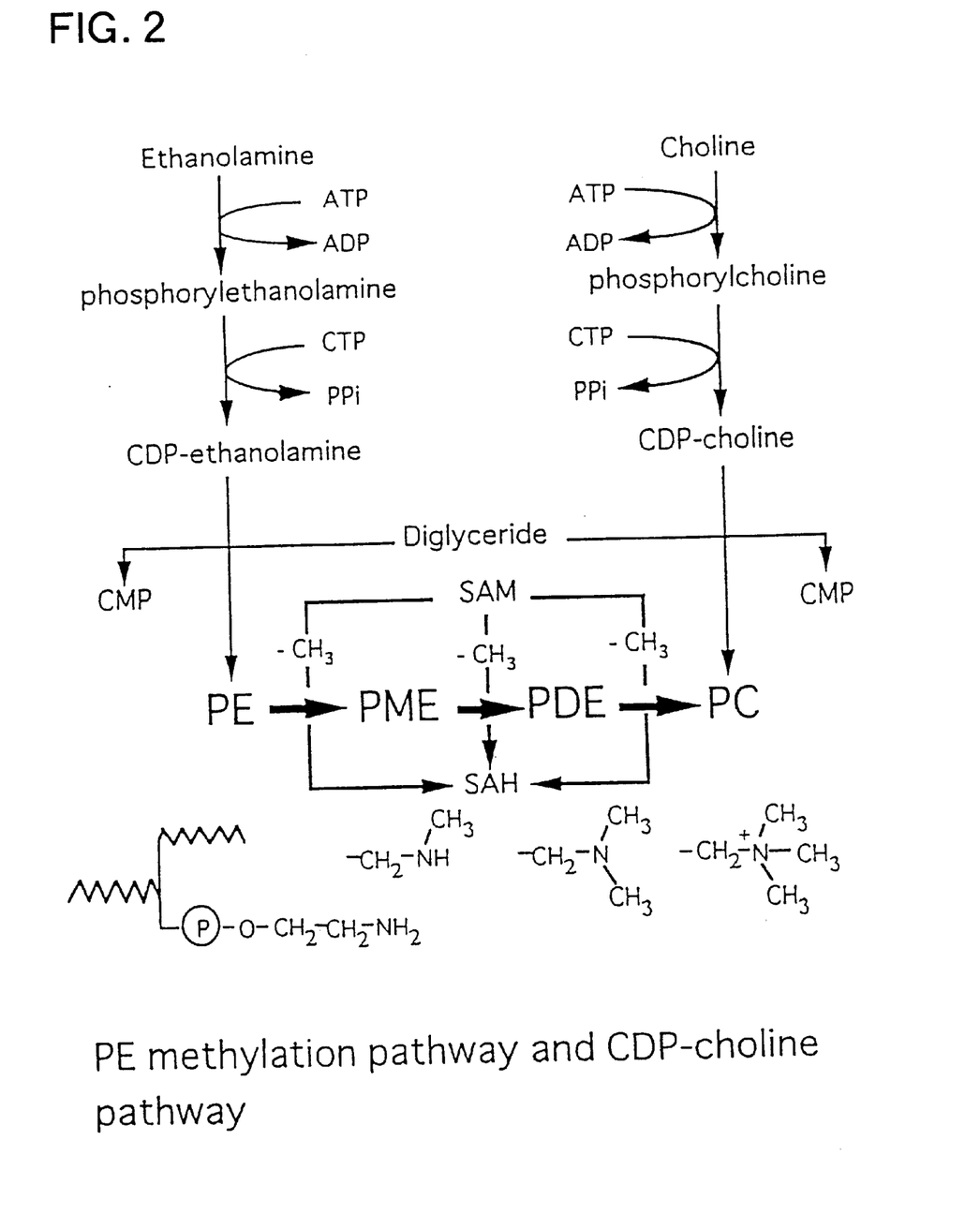
FIG. 2 shows PE methylation and CDP-choline pathways.

Phosphatidylethanolamine (PE) N-methyltransferase is an enzyme which catalyzes the PE N-methylation pathway in phospholipid metabolism, by transferring a methyl group of S-adenosyl-L-methionine to an amino group of PE to synthesize phosphatidylcholine (PC) via two intermediates phosphatidyl N-monomethylethanolamine (PME) and phosphatidyl N,N-dimethylethanolamine (PDE) (see FIG. 2).

This kind of enzyme can be obtained by purification from membrane fractions of bacteria, yeast and rat liver or DNA cloning. Their characteristics have been reported (Arondel et al., J. Biol. Chem., 268: 16002–16008(1993); Kodaki and Yamashita et al., J. Biol. Chem., 262: 15428 (1987); Cui et al., J. Biol. Chem., 268: 16655–16663 (1993)). Two distinct enzymes catalyze the PE N-methylation pathway in the metabolism of the yeast *Saccharomyces cerevisiae* while only one enzyme catalyzes synthesis of PC from PE in the metabolisms of the bacteria *Zymomonas mobilis*, *Rhodohacter spheroides* and rat liver. Thus, phosphatidylethanolamine N-methyltransferase is a very useful enzyme for synthesis of PC with high optical purity.

PC is widely used as a main component of liposomal membrane in the studies of, for example, biomembrane or reconstituted membranes. Moreover, PC is contained in various foods as digestible surfactant, and plays an important role in medical and pharmaceutical fields as a component of microcapsule for drugs, low molecular weight compounds or the like. Although phosphatidylethanolamine N-methyltransferases useful for synthesis of PC have been found in bacteria, yeast and rat, most of enzymes are less thermostable since they are derived from mesophilic organisms so that they are not suitable for synthetic reactions that further require use of organic solvents and the like.

Archaea including the genus Pyrococcus contain as a main lipid an ether-type lipid in which glycerol binds to hydrocarbon chain via ether-bond, not via ester-bond. On the other hand, any ester-type lipids, which are main lipids in bacteria and eukaryotes, have not been found in archaea. Accordingly, it has been suggested that phosphatidylethanolamine N-methyltransferase derived from archaea may be associated with synthesis of choline residue contained in ether-type lipid, and thus the enzyme is expected to be useful for synthesis of archaetidyl choline, caldarchaetidyl choline and the like which are remarked as novel components of liposomal membranes. It can be assumed that discovery of an archaea-derived thermostable phosphatidylethanolamine N-methyltransferase that is active in organic solvent will make it possible to develop a novel process for synthesizing polar lipid with high optical purity by introducing a methyl group into PE, archaetidyl ethanolamine, caldarchaetidyl ethanolamine and the like, which are important as lipid components of model membranes.

However, no phosphatidylethanolamine N-methyltransferase that is active under an extreme environment has been obtained and there has been a strong demand for such enzyme.

An object of the present invention is to provide a thermostable phosphatidylethanolamine N-methyltransferase.

Another object of the present invention is to provide a gene encoding the thermostable phosphatidylethanolamine N-methyltransferase as well as a process for producing the enzyme using the gene.

For the above-described purposes, the present inventors noted hyper-thermophilic archaea which are viable at 90–100° C., particularly *Pyrococcus horikoshii,* and obtained a gene that was assumed to show phosphatidylethanolamine N-methyltransferase activity from their genome sequence. Further, the inventors produced the enzyme from the gene by using *E. coli* and confirmed that the enzyme was stable at a high temperature (90° C. or higher) and had phosphatidylethanolamine N-methyltransferase (hereinafter occasionally referred to as PE N-methyltransferase) activity, thus accomplishing the present invention.

This specification includes all or part of the contents as disclosed in the specification and/or drawings of Japanese Patent Application No. 11-89312 (filed Mar. 30, 1999), which is a priority document of the present application.

SUMMARY OF THE INVENTION

In summary, the present invention relates to the following (1)–(7):

(1) a thermostable enzyme derived from a hyper-thermophilic archaeon *Pyrococcus horikoshii*, having phosphatidylethanolamine N-methyltransferase activity and an optimum temperature of 90° C. or higher;

(2) a thermostable enzyme derived from a hyper-thermophilic archaeon, wherein the enzyme has phosphatidylethanolamine N-methyltransferase activity and the following properties:
  (a) optimum temperature: 90° C. or higher;
  (b) substrate specificity: when the enzyme acts on phosphatidyl N-monomethylethanolamine as substrate, incorporation of a methyl group is detected in only phosphatidyl N,N-dimethylethanolamine but not in phosphatidylcholine, while when the enzyme acts on phosphatidylethanolamine as substrate, incorporation of a methyl group is detected in only phosphatidyl N-monomethylethanolamine and phosphatidyl N,N-dimethylethanolamine but not in phosphatidylcholine;
  (c) optimum pH: about 8–9;

(3) a thermostable enzyme having phosphatidylethanolamine N-methyltransferase activity, selected from the group consisting of:
  (a) a protein having the amino acid sequence of SEQ ID NO: 1; or
  (b) a protein having deletions, substitutions or additions of one or more amino acids in the amino acid sequence of SEQ ID NO: 1, and having phosphatidylethanolamine N-methyltransferase activity and an optimum temperature of 90° C. or higher;

(4) DNA encoding the thermostable enzyme of (1) or (2) above;

(5) DNA encoding the thermostable enzyme of (3);

(6) DNA of (5) having the nucleotide sequence of SEQ ID NO: 2;

(7) a process for producing the thermostable enzyme described in any one of (a)–(c), comprising the steps of constructing an expression vector containing DNA described in (4), (5) or (6), transforming a host cell with the vector, culturing the transformed host cell in medium and collecting thermostable enzyme produced.

DETAILED DESCRIPTION OF THE INVENTION

In accordance with a first aspect of the present invention, a thermostable enzyme derived from *Pyrococcus horikoshii*, which has an optimum temperature of 90° C. or higher and phosphatidylethanolamine N-methyltransferase activity, is provided.

In one embodiment of the present invention, gene encoding the enzyme of interest was obtained from *Pyrococcus horikoshii*, (Deposition No: JCM9974) by cDNA cloning of its genome, the gene was incorporated in a suitable expression vector which was then used to transform a host cell to express the gene, and phosphatidylethanolamine N-methyltransferase of interest was collected.

Enzyme of the present invention showed no decrease in their activity after retention at 90° C. for 4 hours, and kept 76% of the activity even after retention at 100° C. for 2 hours. Conventionally, such kind of enzyme with thermostability has not at all been known and thus it was surprising to find this high thermostability.

In a second aspect of the present invention, another thermostable enzymes derived from hyper-thermophilic archaea having phosphatidylethanolamine N-methyltransferase activity are provided.

The enzyme is characterized by the following properties: an optimum temperature of 90° C. or higher; an optimum pH of about 8–9, particularly about 8.5; and substrate-specificity distinct from that of any of conventionally-known PE N-methyltransferases. In other words, when the enzyme acts on phosphatidyl N-monomethylethanolamine (PME) as substrate, incorporation of a methyl group is detected in only phosphatidyl N,N-dimethylethanolamine (PDE) but not in phosphatidylcholine (PC), while when the enzyme acts on phosphatidylethanolamine (PE) as substrate, incorporation of a methyl group is detected in only phosphatidyl N-monomethylethanolamine (PME) and phosphatidyl N,N-dimethylethanolamine (PDE) but not in phosphatidylcholine (PC). On the other hand, when using PE as the substrate and conventional PE N-methyltransferase derived from the purple non-sulfur bacterium Rhodobacter, the yeast *S. cerevisiae* or rat liver as the enzyme, incorporation of a methyl group is detected in PME, PDE and PC. The substrate specificity of these enzyme is thus apparently different from that of the present enzyme. The enzyme of the present invention having the above-described properties has not been found and thus, the present enzyme is a novel enzyme in this point.

Hyper-thermophilic archaea herein include any archaea that are viable at an optimum temperature of about 90° C. or higher and contain an ether-type lipid as main lipid in which glycerol binds to hydrocarbon chain via ether-bond. Such hyper-thermophilic archaea include, but are not limited to, those which belong to the genus Pyrococcus such as *Pyrococcus horikoshii*, *Pyrococcus furiosus* and *Pyrococcus abyssi*, the genus Aeropyrum such *Aeropyrum pernix*, the genus Sulfolobus and others.

Sulfur-metabolizing hyper-thermophilic archaea which belong to the genus Pyrococcus, particularly *Pyrococcus horikoshii* (Deposition No: JCM9974) will be illustrated showing preparation of a thermostable enzyme having phosphatidylethanolamine N-methyltransferase activity derived from the specific archaeon in the Examples below. This enzyme has the above-described optimum temperature, substrate specificity and optimum pH, and has a molecular weight ranging 23,000–25,000 Da. The amino acid sequence of the enzyme and DNA sequence encoding the amino acid sequence determined by cDNA cloning were shown as SEQ ID NOS: 1 and 2 in the SEQUENCE LISTING, respectively.

According to a third aspect of the present invention a thermostable enzyme having phosphatidylethanolamine N-methyltransferase activity is provided, which is either of the following protein (a) or (b):

(a) a protein having the amino acid sequence as shown in SEQ ID NO: 1; and (b) a protein having phosphatidylethanolamine N-methyltransferase activity and an optimum temperature of 90° C. or higher, and having deletions, substitutions or additions of one or more amino acids in the amino acid sequence as shown in SEQ ID NO: 1.

Proteins of the present invention include those described in (b) though the manner and extent of the mutation are not limited as long as the protein has PE N-methyltransferase activity and an optimum temperature of 90° C. or higher. Such mutation of one or more amino acids may be generated by using various techniques such as Kunkel technique, PCR (polymerase chain reaction) method and site-directed mutagenesis such as oligonucleotide site-directed mutagenesis or casette mutagenesis based on, for example, DNA sequence encoding the protein of (a) above (see, for example Mark et al., Proc. Natl. Acad. Sci. USA, 81: 5662–5666, 1984; PCT WO85/00817; Ausubel et al., Short Protocols In Molecular Biology, Third Edition, A Compendium of Methods from Current Protocols in Molecular Biology, John Wiley & Sons, Inc.,[1992]).

According to a fourth aspect of the present invention, DNA encoding the above-described thermostable enzyme of the present invention is provided. Particular examples of the DNA are those encoding protein of (a) or (b) above, e.g., a DNA having the nucleotide sequence of SEQ ID NO: 2 and mutants thereof.

The DNA of the present invention can be obtained from hyper-thermophilic archaea which produce the present enzyme by using genome cloning or cDNA cloning method (J. Sambrook et al., Molecular Cloning, A Laboratory Manual, Second Edition, Cold Spring Harbor Laboratory Press, 1989). For example, a genomic library or cDNA library may be prepared based on a genomic gene from hyper-thermophilic archaea, and a clone containing DNA encoding the present enzyme may be selected by hybridization using a suitable probe. Alternatively, DNA of interest may be obtained by direct PCR amplification of the DNA using any suitable primer. Restriction map of the DNA may be prepared by digesting the DNA with various restriction enzymes so that DNA of interest can be excised based on the restriction map as required. Alternatively, it may be confirmed that the obtained DNA is the DNA of interest by sequencing its nucleotide sequence using a conventional method such as deoxy-method (Sanga et al., Proc. Natl. Acad. Sci. USA, 74:5463, 1977). Alternatively, object DNA can be synthesized in a DNA synthesizer based on the determined DNA sequence.

Probes and primers as used herein can be prepared based on the amino acid sequence of SEQ ID NO: 1, the nucleotide sequence of SEQ ID NO: 2 or complementary sequences thereof. These probes and primers comprise 5 or more nucleotides, normally 5–60 nucleotides, and preferably 15–30 nucleotides. Desirably, these have a highly conserved region. Hybridizing conditions may be appropriately determined by taking into account various parameters such as melting temperature of the DNA and ionic strength. Preferably, hybridization and washing may be carried out under stringent conditions. Normally, 20 or more rounds of PCR amplification may be performed. The amplification cycle may consists of the following steps of: denaturing the double stranded DNA (for example, at 94° C. for 15–30 sec); annealing the single-stranded template DNA and a primer (for example, at 55° C. for 30 sec to 1 min); and extending the primer under coexistence of a thermostable DNA polymerase and 4 kinds of substrates (dNTPs) (for example, at 72° C. for 30 sec to 10 min). PCR conditions may be appropriately varied depending on the concentration of template DNA and the size of amplified fragment, for example. PCR method is disclosed in, for example, Protein, Nucleic Acid and Enzyme, ISSN 0039-9450, Vol. 41, No. 5 (1996), "Frontier PCR", April (1996).

According to a fifth aspect of the present invention, a process for producing the above-described thermostable enzyme is provided, which comprises the steps of constructing an expression vector containing the above-described DNA, transforming a host cell with the vector, culturing the transformed host cell in a medium, and collecting the thermostable enzyme produced.

The enzyme of the present invention may be produced in either secretory or non-secretory manner. When the enzyme is secreted, DNA sequence encoding any signal peptide may be ligated to an upstream side of the enzyme gene. On the other hand, when produced in non-secretory manner, it can be obtained as a fused protein with a sequence which facilitates isolation of the enzyme (for example histidine-tag) or a sequence which facilitates cleavage/separation of matured proteins. Expression vectors to be used include those which can autonomously replicate in prokaryotic or eukaryotic host cells or can be incorporated in a chromosome as well as contain a promoter at an appropriate position such that the DNA can be transcribed. Such vectors include viral vectors, cosmid, plasmids and phages. Vectors must contain promoters. Optionally, they may also contain a selective marker, an enhancer, a ribosome-binding site, a replication origin, a terminator and a polylinker. Any expression vectors which are commercially available or those disclosed in literatures may be preferably selected.

Examples of expression vector are as follows: vectors for prokaryotic cells such as pBtrp2, pBTac1, pBTac2 (Boehlinger Mannheim), pSE280 (Invitrogen), pQE series (Promega), pET series (Novagen) and pBluescript II series (Stratagene); vectors for eukaryote such as pHS19, pHS15, pG-1 pXT1, pSG5 (Stratagene), pSVK3, pBPV and pMSG (Pharmacia) for yeast cells, pcDNAI, pcDM8 (Funakoshi Co., Ltd.), pcDNAI/Amp, pREP4 (Invitrogen) for animal cells, pVL1392, pVL1393, pBlueBacIII (Invitrogen) for insect cells, and Ti pasmid and tobacco mosaic virus vector for plant cells.

Promoters include, but are not limited to: promoters for prokaryote such as trp promoter, lac promoter, $P_L$ promoter, $P_R$ promoter, SPO1 promoter, SPO2 promoter and pen P promoter; promoters for yeast cells such as PHO5 promoter, PGK promoter, GAP promoter, ADH promoter, GPD promoter, gal 1 promoter and gal 10 promoter; promoters for animal cells such as those of IE (immediate early) gene of cytomegalovirus, early promoter of SV40, retrovirus promoter, heat-shock promoter and mammary gland cell-specific promoter; and promoters for plant cells such as 35S promoter of cauliflower mosaic virus and rice actin 1 promoter.

Host cells include prokaryotic and eukaryotic cells. Example of prokaryotic cells are those of microorganisms which belong to the genera Escherichia, Serratia, Bacillus and Pseudomonas. Examples of eukaryotic cells are: yeast cells which belong to the genera Saccharomyces, Schizosaccharomyces and Pichia; animal cells such as human fetus nephrocytes, Chinese hamster ovary (CHO) cells and mouse myeloma cells; insect cells such as Spodopterafrugiperda ovary cells and Trichoplusiani ovary cells; and plant cells such as dicotyledone and monocotyledone.

Transformation techniques include calcium-ion method, calcium phosphate method, lithium acetate method, electroporation, spheroplast, protoplast, lipofection and agrobacterium-mediated method. Transformation technique may be selected depending on the host cell to be used.

After culturing the host cells transformed according to any of above-described technique under suitable culture conditions for the selected cell, a protein of interest may be separated and purified using any conventional protein-separation/purification method. When produced in a secretory manner, the enzyme can be directly purified from the medium. On the other hand, when produced in non-secretory manner, the enzyme may be purified by, for example, separating the cells by centrifugation, suspending them in a buffer A, disrupting the cells in the suspension by ultrasonication, French press, Manton Gaulin homogenizer or others to obtain a cell-free extract solution, and purifying the enzyme therefrom. Purification of the enzyme from the medium or extract solution may be performed by techniques such as solvent extraction, salting-out, demineralization, precipitation with organic solvent, ultrafiltration, ion-exchange chromatography, hydrophobic interaction chromatography, HPLC, gel filtration chromatography, affinity chromatography, electrophoresis and isoelectric-focusing electrophoresis alone or in combination.

In the following Examples, the present enzyme was produced by PCR-amplification and extraction of a gene suspected to encode the enzyme activity of the present invention from the genes of the sulfur-metabolizing-thermophilic archaeon Pyrococcus horikoshii (Deposition No: JCM9974), followed by insertion of the gene into protein-expressing plasmid pET15b which was then introduced into E. coli. Produced enzyme was heated and isolated by purification using column chromatography. The purified enzyme was found to be a protein having a molecular weight of 23,377 Da, which was PE N-methyltransferase. Thermostability of the enzyme was evaluated by obtaining membrane fractions from transformed E. coli containing the enzyme gene, retaining the fractions at 100° C. and determining the remaining-activity after a pre-determined period of time. Even after 2 hours 76% of the activity remained. Even after 4 hours the enzyme activity was stable with no decrease at 90° C. Optimum pH of the activity was about pH 8–9, particularly about 8.5, and the optimum temperature was over 90° C. at pH8.0.

Experimental

The present invention will be described in more detail by means of Examples though the present invention is not intended to be limited thereto.

Example 1

Cloning and Sequencing of PE N-methyl tranferase Gene Derived from the Thermophilic Archaeon *Pyrococcus horikoshii* (Deposition No: JCM9974)

1. Culturing Bacteria

The thermophilic archaeon *Pyrococcus horikoshii* (Deposition No: JCM9974; RIKEN, The Institute of Physical and Chemical Research, Wako, Japan) was cultered as follows:

NaCl (13.5 g), $Na_2SO_4$ (4 g), KCl (0.7 g), $NaHCO_3$ (0.2 g), KBr (0.1 g), $H_3BO_3$ (30 mg), $MgCl_2.6H_2O$ (10 g), $CaCl_2$ (1.5 g), $SrCl_2$ (25 mg), resazurin solution (1.0 ml, 0.2 g/L), yeast extract (1.0 g) and Bacto-peptone (5 g) were dissolved in 1 L of water. The solution was adjusted to pH 6.8 and sterilized under pressure. Subsequently, element sulfur sterilized by dry-heating was added to the medium to 0.2% and the medium was made anaerobic by saturation with argon and JCM9974 cells were inoculated thereon. It was confirmed that the medium became anaerobic by adding $Na_2S$ solution and determining that pink color of the resazurin solution disappeared in the culture solution by addition of $Na_2S$. The culture solution was cultured at 95° C. for 2–4 days and then cells were collected by centrifugation.

2. Preparing Chromosomal DNA

Chromosomal DNA of JCM9974 was prepared as follows: After culture, cells were collected by centrifugation at 5000 rpm for 10 minutes, washed (2x) with 10 mM Tris (pH7.5) 1 mM EDTA solution and enclosed in InCert Agarose (FMC BioProducts) block which was then treated with 1%N-lauroylsarcosine, 1 mg/ml protease K solution to separate and prepare the chromosomal DNA into Agarose block.

3. Preparing Library Clone Containing Chromosomal DNA

The chromosomal DNA obtained in 2 above was partially digested with restriction enzyme HindIII, and fragment having about 40 kb length was then prepared by agarose gel electrophoresis. The DNA fragment was ligated with Bac vector pBAC108L (available from Stratagene) or pFOS1 (Stratagene) completely digested with restriction enzyme HindIII using T4 ligase. When the former vector was used, DNA obtained by ligation was immediately introduced into *E. coli* by electroporation. When the latter vector pFOS1 was used, DNA obtained by ligation was incorporated into a λ phage particle in vitro using GIGA Pack Gold (available from Stratagene), and in turn the particle was introduced into a *E. coli* cell by infection. The populations of antibiotic chloramphenicol resistant *E. coli* obtained as described above were designated as BAC and Fosmic libraries. Suitable clones were selected from the libraries for covering the chromosome of JCM 9974, and then aligned (see Y. Kawarabayasi et al., DNA Research. 5:55 (1998)).

4. Sequencing of Each BAC or Fosmid Clone

Sequencing of the aligned BAC or Fosmid clone was performed as follows. Each BAC or Fosmid clone DNA collected from the *E. coli* cell was fragmented by ultrasonication, and DNA fragments having lengths of 1 kb and 2 kb were collected. These fragments were incorporated into plasmid vector pUC118 at the HincII-restriction site to prepare shot-gun clones at 500 shotgun clones per BAc or Fosmid clone. Each shotgun clone was sequenced by Automatic-Sequence Reading Machine Type 373 or 377 (available from Perkin-Elmer Corp., ABI Corp.). Nucleotide sequence obtained from each shotgun clone was ligated and edited using a nucleotide sequence auto-ligating software (Sequencher) to determine the complete nucleotide sequence of each BAC or Fosmid clone.

5. Identifying PE N-methyltransferase Gene

Figure 1:
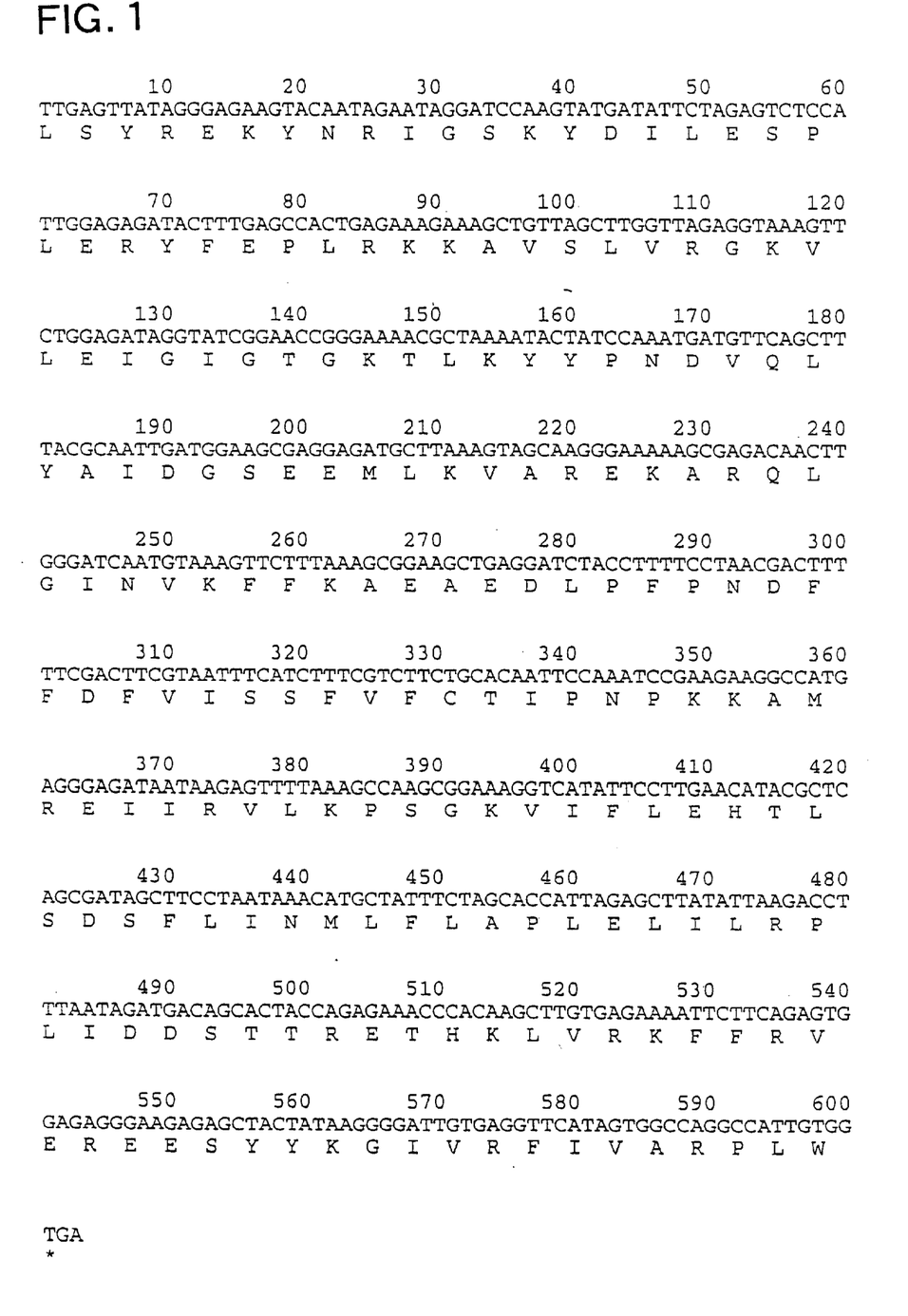
FIG. 1 shows the amino acid sequence (SEQ ID NO:1) of the thermostable phosphatidylethanolamine N-methyltransferase and the nucleotide sequence (SEQ ID NO:2) of the gene encoding the enzyme.

The nucleotide sequence determined for each BAC or Fosmid clone as described above was analyzed using a large computer to determine the nucleotide sequence of PE N-methyltransferase coding gene (SEQ ID NO: 2, FIG. 1) and the amino acid sequence of the enzyme (SEQ ID NO: 1, FIG. 1). Homology search was performed for the amino acid sequence of the enzyme using database to find that the amino acid sequence of the present enzyme had 27.6% homology to that of PE N-methyltransferase from *Rhodobacter sphaeroides*. The amino acid sequence of the enzyme from *R. sphaeroides* contained a region having high homology to those of other methyltransferases (RGGRVLEVG) (Arondel et al., J. Biol. Chem., 268: 16002–16008 (1993)), and *P. horikoshii* enzyme also contained the similar region. However, no homology was found at amino-acid level between *P. horikoshii* enzyme and PE N-methyltransferase derived from yeast or rat liver.

Example 2

Constructing Expression Plasmid and Gene Expression

1. Constructing Expression Plasmid

For the purpose of constructing restriction NdeI- and BamHI-sites at either ends of the structural gene region of PE N-methyltransferase, the following DNA primers were synthesized to introduce the restriction sites at the ends of the structural gene region by PCR.

Upper primer (SEQ ID NO: 3)
5'-TTTTGAATTCTTACATATGAGTTATAGGGAGAAG-TACAATAGAATAGGGTCCAAGTATGATATTCTA-3'

Lower primer (SEQ ID NO: 4)
5'-TTTTGGTACCTTTGGATCCTTAAGCCATCGATCA-CCACAATG-3'

After PCR reaction, the DNA was completely digested with restriction enzymes NdeI and BamHI (at 37° C. for 2 hours), followed by purification of the structural gene.

After digestion and purification of pET15b (available from Novagen) with restriction enzymes NdeI and BamHI, resultant fragments were ligated with the above-described structural gene at 16° C. for 2 hours using T4 ligase. Portion of the ligated DNA was introduced into a competent cell of *E. coli* XL2-Blue MRF' to obtain colonies of transformants. Then, expression plasmid was purified from the formed colonies by alkaline process.

2. Expression of Recombinant Gene

Competent cells of *E. coli* BL21 (DE) (available from Novagen) were lysed and 0.1 mL of the lysate was transferred to a Falcon tube. Then, solution of expression plasmid (0.005 mL) purified in 1 above (0.005 mL) was added thereto, left for 30 minutes in ice, and then subjected to heat-shock at 42° C. for 30 seconds. Next, the cells were added with SOC medium (0.9 mL) and cultured while shaking at 37° C. for 1 hour. Subsequently, and appropriate amount of the cells were inoculated on an ampicillin-containing 2YT agar plate and cultured at 37° C. overnight to obtain transformant. The transformant *E. coli* (ID No; *E. coli* BL21 (DE3)/pET15b/PEM trans) was deposited as FERM P-17349 with National Institute of Bioscience and Human-Technology, Agency of Industrial Science and Technology (1-3, Higashi 1-chome, Tsukuba-shi, Ibaraki-ken, 305-8566, Japan) on Mar. 29, 1999.

Obtained transformant was cultured in an ampicillin-containing-2YT medium (2 L) until abosrption at 600 nm reached 1, then added with IPTG(Isopropyl-β-D-thiogalactopyranoside) and further cultured for 6 hours to express PE N-methyltransferase gene. After culture, cells were collected by centrifugation at 6,000 rpm for 20 minutes.

Example 3

Purification of Thermostable PE N-Methyltransferases from Membrane Fraction

1. Preparing Membrane Fraction

Cells were added with IPTG, cultured for 5 hours and then collected. The collected cells were washed (2×) with iced-cooled Buffer A (80 mM Tris-HCl, 10% glycerol, 20 mM L-cysteine, pH8.5) and suspended in Buffer A at 2 ml Buffer A/g wet cells. Cells in the suspension was disrupted by ultra-sonication at 180 w for 4 minutes, and undisrupted cells were removed from the disruption solution by centrifugation at 9000×g for 10 minutes. Obtained supernatant was centrifuged at 39,000×g for 1 hour to give the residue as membrane fraction.

Prepared membrane fraction was suspended in 80 mM Tris-HCl buffer (pH8.5) and immediately solubilized.

2. Purifying Thermostable Enzyme (1) Solubilization

Surfactant Triton X-100 was added to the prepared membrane fraction to a final concentration of 1% and stirred for 1 hour under ice-cooling by a Teflon homogenizer for solubilization. Insoluble membrane fraction was removed by ultra-centrifugation (105,000×g, 1) to give supernatant as solubilized fraction. The obtained solubilized fraction was diluted (25×) with the above-described buffer A to Triton X-100 concentration of 0.04%, and subjected to DEAE-Sepharose CL-6B (Pharmacia Fine Chemical Corp.) column chromatography.

(2) DEAE-Sepharose CL-6B Column Chromatography

Solubilized fraction was applied to a DEAE-Sepharose CL-6B column (Pharmacia Fine Chemical Corp.) equilibrated with buffer A. After flow-through protein fractions completely flowed out, the solubilized fractions were washed with buffer A and eluted with linear gradient of 0.5M NaCl. Consequently, it was found that the enzyme activity was eluted at around 0.3M. These active fractions were collected, dialyzed against buffer B (50 mM $NaH_2PO_4$, 300 mM NaCl, 10% glycine, pH8.0) for 12 hours and then subjected to Ni-NTA agarose column chromatography.

(3) Ni-NTA Agarose Column Chromatograph

The dialyzed active fractions were added to Ni-NTA agarose column (Quiagen) balanced with buffer B. After flow-through protein fractions completely flowed out, the active fractions were washed with 20 mM imidazole-containing buffer A and eluted with 200 mM imidazole-containing buffer A. Little enzyme activity was detected in the flow-through fractions and localized in eluted fractions. Homogeneity were examined by SDS-polyacrylamide gel electrophoresis. The purified enzyme sample showed a single band.

Example 4

Characterization of Enzyme

1. Analysis Condition (1) Assay of PE N-methyltransferase Activity

PE N-methyltransferase enzyme activity was determined by incorporation of a methyl group of [$^{14}$C-methyl]-S-adenosyl-L-methionine (SAM) into PDE. Reaction system contained 1.7 μM [$^{14}$C-methyl]-SAM (59.8 μCi/μmol, New England Nuclear), 58 μM PME (Avanti Polar Lipid), 0.04% Triton X-100 and enzyme solution in 1 ml of buffer A. Reaction was carried out at 90° C. for 30 minutes. Reaction was stopped by adding chloroform-methanol-1N hydrochloric acid (1:2:0.2 v/v) mixture solution (4 ml), and lipid fractions in the reaction system were extracted by Bligh-Dyer method. The extracted lipid fractions were added with 5 μg of PDE (Avanti Polar Lipid) as the reaction product marker, and separated by one-dimensional thin-layer chromatography on a silica gel 60 plate (Merck) using chloroform-methanol-water (65:25:4, v/v). Lipid was developed in iodine vapor and spot which corresponds to PDE was scraped out together with the silica gel, and radioactivity thereof was determined using a liquid scintillation counter (LSC-700, Aloka). The enzyme activity 1 U is defined as the amount (pmol) of PDE synthesized per 1 minute.

(2) Identifying the Reaction Product

The reaction products obtained using the enzyme were separated by one-dimensional thin-layer chromatography, and examined by RI scanner (Aloka) after color development of lipids in iodine vapor to find regions with higher radioactivity. These portions were compared with iodine-vapor-developed portion of standard PDE or PC (available from Sigma) to identify reaction products.

(3) Optimum Temperature and Optimum pH

Incorporation of radio-activity into PDE was assayed at a variety of temperatures from 60° C. to 100° C. under the above-reaction conditions and the optimum temperature was determined from the relative activities. Optimum pH was determined from the variation of relative activities determined at various pH values from 6.5 to 9.5 of the enzyme solution using 50 mM Tris-HCl buffer.

(4) Thermostability

Thermostability of the enzyme was determined by keeping membrane fractions prepared from the transformed *E. coli* cells at 90° C. and 100° C. for a certain period of time and determining the remaining activities under the above-described reaction conditions.

2. Properties of the Enzyme (1) Chemical Property of the Protein

The present enzyme with 200 amino acid residues and had a deduced molecular weight of 23,377 Da.

(2) Substrate Specificity

Figure 3:
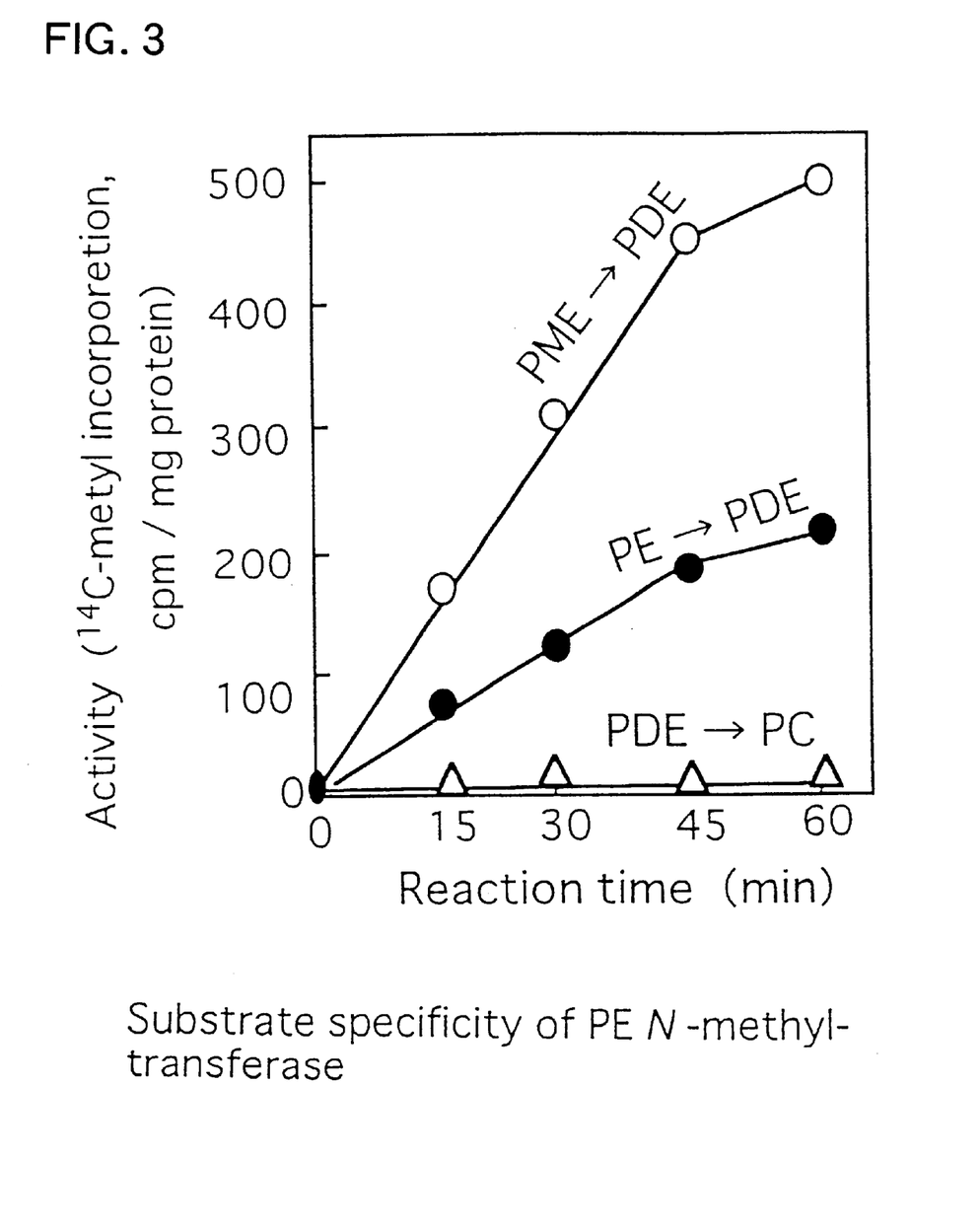
FIG. 3 shows the substrate specificity of the thermostable phosphatidylethanolamine N-methyltransferase.

As shown in FIG. 3, incorporation of a methyl group from SAM was detected in only PDE but not in PC among the products obtained when using PME as substrate. When PE was used as substrate, PME as well as PDE were detected though PC was not. Further, when PDE was used as substrate, no distinct reaction product was detected. Accordingly, it can be assumed that the enzyme activity catalyzes the first and second steps of PE N-methyl pathway to synthesize PDE. The relative ratio of the enzyme activity for PE to PME was 1:2.5. Table 1 shows comparison of properties of the enzyme derived from *P. horikoshii* with those of PE N-methyltransferases derived from other organisms. *P. horikoshii* enzyme acted on PE and PME as substrates, to synthesize PDE, though it did not show any activity for PDE. Accordingly, the *P. horikoshii* enzyme had different substrate-specificity from any other PE N-methyltransferases which had been reported (see Table 1).

TABLE 1

Properties of Cloned Phosphatidylethanolamine N-methyltransferases

| Origin | Molecular Weight (Number of Amino Acid Residues) | Amino Acid Homology | PE N-Methylation Reaction Catalyzed by the Enzyme | Optimum Temperature | Reported by |
|---|---|---|---|---|---|
| Hyper thermophilic archaeon, Pyrococcus horikoshii | 23,377 (200) |  | PE → PME → PDE | Very high (90° C.) | The present invention |
| Purple nonsulfur bacteria, Rhodobacter | 22.9K (203) | 27.6% | PE → PME → PDE → PC | Normal (30° C.) | Arondel et al. (1993) |
| Yeast, S. cerevisiae | 23,150 (206) |  | PE → PME → PDE → PC | Normal (30° C.) | Kodaki and Yamashita et al. (1987) |
| Rat liver | 22.3K (199) | 44.0% | PE → PME → PDE → PC | Normal (30° C.) | Cui et al. (1993) |

(3) Optimum Temperature and pH

Figure 4:
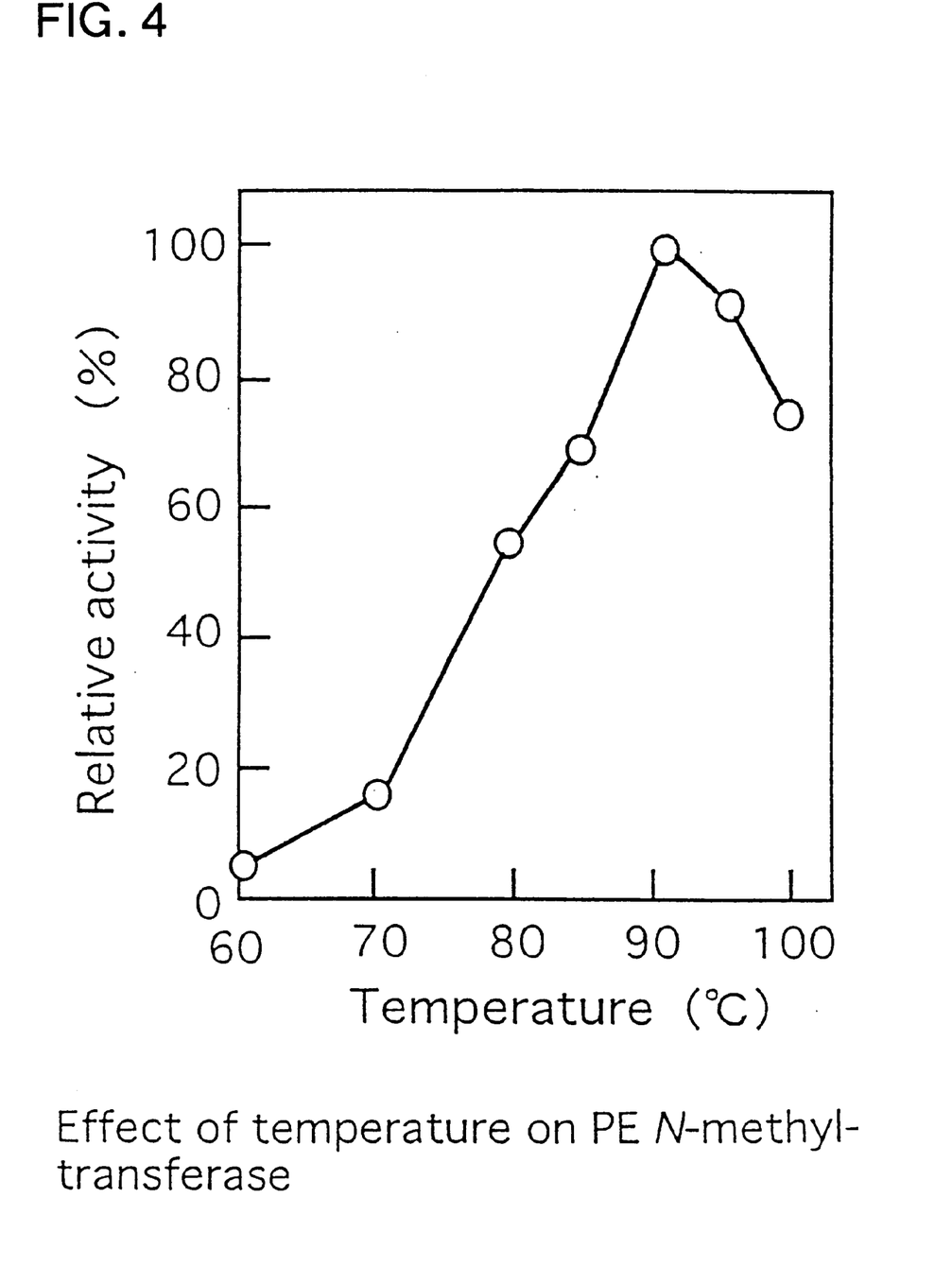
FIG. 4 shows the effect of temperature on the activity of the thermostable phosphatidylethanolamine N-methyltransferase.
Figure 5:
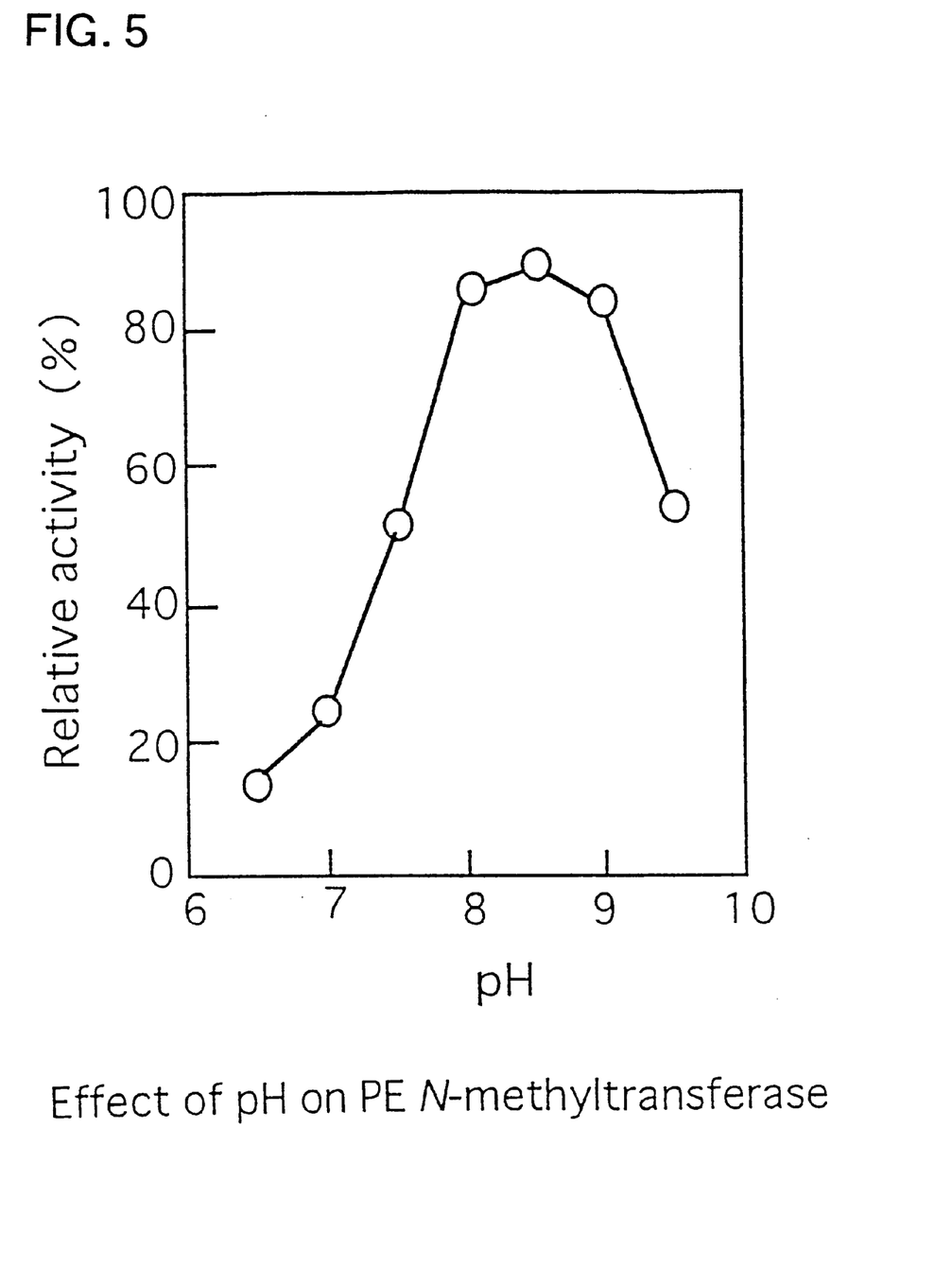
FIG. 5 shows the effect of pH on the activity of the thermostable phosphatidylethanolamine N-methyltransferase.

Optimum temperature was proved to be 90° C. or higher as shown in FIG. 4. Also, optimum pH of the enzyme was proved to be about 8–9, particularly about 8.5 as shown in FIG. 5.

(4) Thermostability

Figure 6:
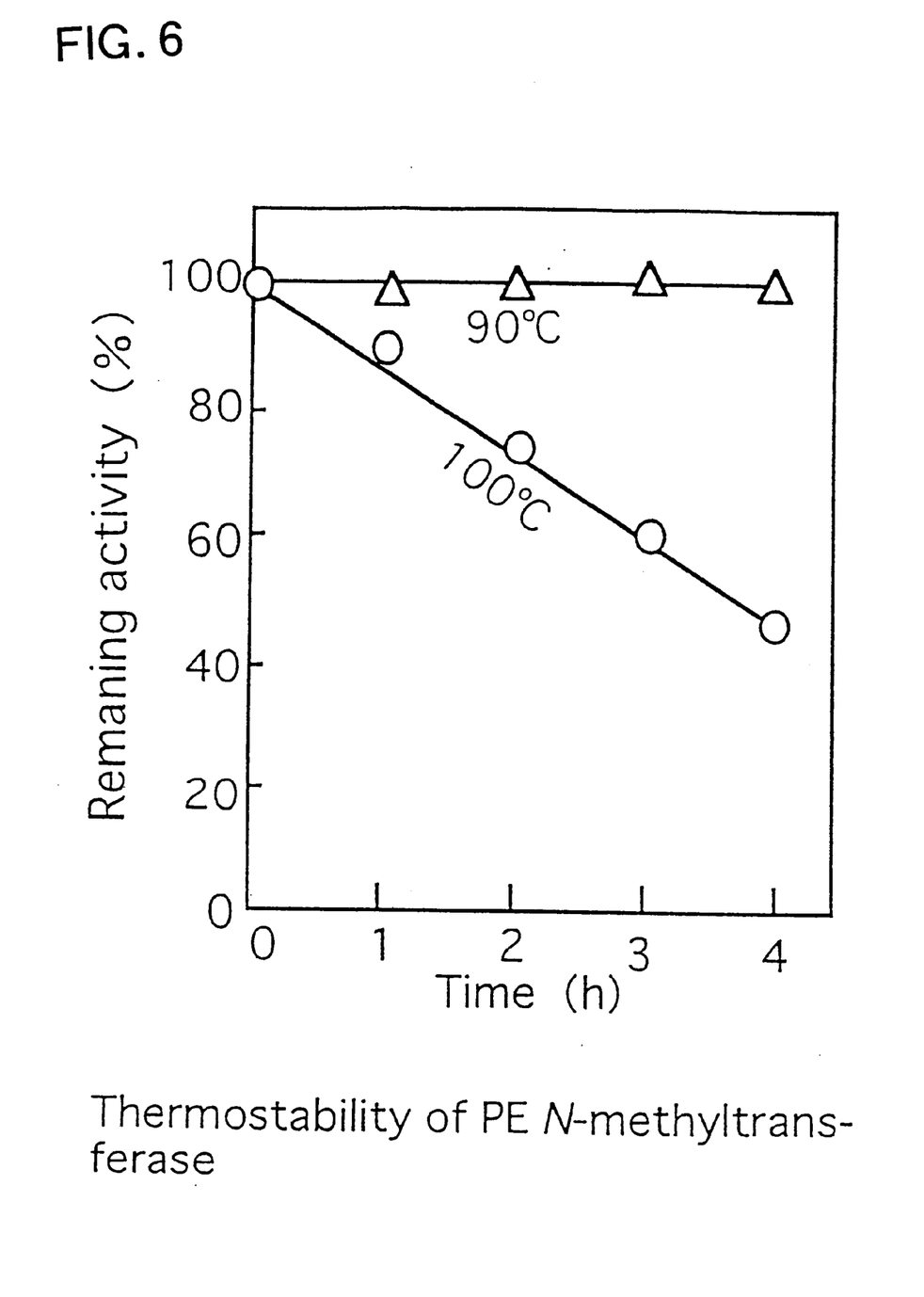
FIG. 6 shows the thermostability of the thermostable phosphatidylethanolamine N-methyltransferase.

Thermostability of the enzyme was determined by retaining the membrane fraction at 100° C. and assaying the remaining activity after a predetermined period of time. Even after 2 hours 76% of the enzyme activity was remained. At 90° C., the enzyme activity was stable with no decrease even after 4 hours (see FIG. 6).

Effect of the Invention

The present invention can provide a thermostable PE N-methyltransferase having an optimum temperature for reaction of 90° C. or higher. Further, the enzyme has a different substrate-specificity from any other PE N-methyltransferases derived from mesophilic organisms which have been reported. Accordingly, the development of a novel polar lipid with high optical purity will be possible using the present enzyme.

All publications, patents and patent applications cited above are incorporated herein by reference in their entities.

What is claimed is:

1. An isolated thermostable enzyme having phosphatidylethanolamine N-methyltransferase activity, wherein said thermostable enzyme is obtained from the hyperthermophilic archaeon *Pyrococcus horikoshii*, wherein said enzyme has an optimum temperature of about 90° C. to 100° C., and wherein said enzyme comprises amino acid residues 1 to 25 of SEQ ID NO:1.

2. The isolated thermostable enzyme of claim 1, wherein said thermostable enzyme has an optimum pH of about 8 to 9.

3. The isolated thermostable enzyme of claim 1, wherein said enzyme is capable of acting on phosphatidyl N-monomethylethanolamine such that incorporation of a methyl group is detected in only phosphatidyl N,N-dimethylethanolamine, and not in phosphatidylcholine.

4. The isolated thermostable enzyme of claim 1, wherein said enzyme is capable of acting on phosphatidylethanolamine, such that incorporation of a methyl group is detected only in phosphatidyl N-monomethylethanolamine and phosphatidyl N,N-dimethylethanolamine, and not in phosphatidylcholine.

5. The isolated thermostable enzyme of claim 1, wherein said enzyme is encoded by the nucleic acid sequence of SEQ ID NO:2.

6. The isolated enzyme of claim 1, wherein said enzyme is encoded by the nucleic acid sequence of SEQ ID NO:2, and where said enzyme is capable of acting on phosphatidylethanolamine, such that incorporation of a methyl group is detected only in phosphatidyl N-monomethylethanolamine and phosphatidyl N,N-dimethylethanolamine, and not phosphatidylcholine.

7. An isolated thermostable enzyme having phosphatidylethanolamine N-methyltransferase activity, wherein said enzyme is obtained from the hyperthermophilic archaeon *Pyrococcus horikoshii*, and wherein said enzyme has an optimum temperature of about 90° C. to 100° C., and has an optimum pH of about 8 to 9, wherein said enzyme is capable of acting on phosphatidylethanolamine, such that incorporation of a methyl group is detected only in phosphatidyl N-monomethylethanolamine and phosphatidyl N,N-dimethylethanolamine, and not phosphatidylcholine, and wherein said enzyme comprises amino acid residues 1 to 25 of SEQ ID NO:1.

8. An isolated thermostable enzyme having phosphatidylethanolamine N-methyltransferase activity, wherein said enzyme is obtained from the hyperthermophilic archaeon *Pyrococcus horikoshii*, wherein said enzyme has an optimum temperature of about 90° C. to 100° C., and when said enzyme comprises the amino acid sequence of SEQ ID NO:1.

9. The isolated thermostable enzyme of claim 1, wherein said enzyme has said activity at a temperature of from 90° C. to 100° C.

10. The isolated thermostable enzyme of claim 1, wherein said enzyme has said activity at 90° C.

11. The isolated thermostable enzyme of claim 1, wherein said enzyme has said activity at a pH from pH 8 to pH 9.

12. The isolated thermostable enzyme of claim 1, wherein said enzyme activity is at an optimum pH of 8.5.

13. The isolated thermostable enzyme of claim 1, wherein said enzyme is encoded by SEQ ID NO:2.

14. The isolated thermostable enzyme of claim 1, wherein said enzyme is encoded by SEQ ID NO:2, and wherein said enzyme is capable of acting on phosphatidylethanolamine, such that incorporation of a methyl group is detected only in phosphatidyl N-monomethylethanolamine and phosphatidyl N,N-dimethylethanolamine, and not phosphatidylcholine.

15. The isolated thermostable enzyme of claim 1, wherein said enzyme comprises SEQ ID NO:1.

16. An isolated polypeptide sequence comprising SEQ ID NO:1.

17. The isolated polypeptide sequence of claim 16, wherein said polypeptide sequence has phosphatidylethanolamine N-methyltransferase enzyme activity.

18. The isolated polypeptide sequence of claim 17, wherein said polypeptide sequence has said enzyme activity at a temperature from 90° C. to 100° C.

19. The isolated polypeptide sequence of claim 17, wherein said enzyme activity is at an optimum temperature of 90° C.

20. The isolated polypeptide sequence of claim 17, wherein said enzyme activity is unchanged at 4 hours of incubation at 90° C.

21. The isolated polypeptide sequence of claim 17, wherein said enzyme activity at 2 hours at 100° C. is 76% of said enzyme activity at the beginning of incubation of said polypeptide sequence at 100° C.

22. The isolated polypeptide sequence of claim 17, wherein said polypeptide sequence has said enzyme activity at a pH of from pH 8 to pH 9.

23. The isolated polypeptide sequence of claim 17, wherein said enzyme activity has an optimum pH of 8.5.

24. A phosphatidylethanolamine N-methyltransferase enzyme isolated from *Pyrococcus horikoshii*, wherein said enzyme comprises amino acid residues 1 to 25 of SEQ ID NO:1.

25. The phosphatidylethanolamine N-methyltransferase enzyme of claim 24, wherein said enzyme has phosphatidylethanolamine N-methyltransferase enzyme activity at a temperature of from 90° C. to 100° C.

26. The phosphatidylethanolamine N-methyltransferase enzyme of claim 24, wherein said enzyme has phosphatidylethanolamine N-methyltransferase enzyme activity at an optimum temperature of 90° C.

27. The phosphatidylethanolamine N-methyltransferase enzyme of claim 24, wherein said enzyme comprises SEQ ID NO:1.

28. The isolated thermostable enzyme of claim 8, wherein said enzyme has said phosphatidylethanolamine N-methyltransferase activity at a temperature of from 90° C. to 100° C.

29. An isolated thermostable enzyme having phosphatidylethanolamine N-methyltransferase activity, wherein said thermostable enzyme is derived from the hyperthermophilic archaeon *Pyrococcus horikoshii*, and where said enzyme has an optimum temperature of about 90° C. to 100° C., an optimum pH of about 8 to 9, wherein said enzyme comprises amino acids 1 to 25 of SEQ ID NO:2, and said enzyme is capable of acting on phosphatidylethanolamine such that incorporation of a methyl group is detected in phosphatidyl N-monomethylethanolamine and phosphatidyl N,N-dimethylethanolamine, and not phosphatidylcholine, and wherein said enzyme is capable of acting on phosphatidyl N-monomethylethanolamine such that incorporation of a methyl group is detected in phosphatidyl N,N-dimethylethanolamine, and not phosphatidylcholine and not in phosphatidylcholine.

\* \* \* \* \*